(12) United States Patent
Chin

(10) Patent No.: US 6,966,887 B1
(45) Date of Patent: Nov. 22, 2005

(54) TEMPORARY ARTERIAL SHUNT AND METHOD

(75) Inventor: Albert K. Chin, Palo Alto, CA (US)

(73) Assignee: Origin Medsystems, Inc., Santa Clara, CA (US)

(*) Notice: Subject to any disclaimer, the term of this patent is extended or adjusted under 35 U.S.C. 154(b) by 514 days.

(21) Appl. No.: 10/087,089

(22) Filed: Feb. 27, 2002

(51) Int. Cl.[7] .................. A61M 5/00; A61M 25/00; A61F 11/00; A61B 17/08
(52) U.S. Cl. .................. 604/8; 604/523; 604/264; 606/108; 606/156
(58) Field of Search .............. 604/8–10, 523, 604/264, 532, 524, 525; 606/108, 153, 191–93, 606/198, 156, 194, 197, 199, 213, 215; 623/1.1, 623/1.11, 1.44, 1.23; 138/118, 128

(56) References Cited

U.S. PATENT DOCUMENTS

| | | | |
|---|---|---|---|
| 3,993,078 A | 11/1976 | Bergentz et al. | |
| 4,744,364 A | 5/1988 | Kensey | |
| 4,794,928 A | 1/1989 | Kletschka | |
| 4,852,568 A | 8/1989 | Kensey | |
| 5,108,421 A | 4/1992 | Fowler | |
| 5,122,122 A | 6/1992 | Allgood | |
| 5,192,301 A | 3/1993 | Kamiya et al. | |
| 5,222,974 A | 6/1993 | Kensey et al. | |
| 5,258,000 A | 11/1993 | Gianturco | |
| 5,312,435 A | 5/1994 | Nash et al. | |
| 5,330,446 A | 7/1994 | Weldon et al. | |
| 5,342,393 A | 8/1994 | Stack | |
| 5,350,399 A | 9/1994 | Erlebacher et al. | |
| 5,383,896 A | 1/1995 | Gershony et al. | |
| 5,383,897 A | 1/1995 | Wholey | |
| 5,395,383 A | 3/1995 | Adams et al. | |
| 5,413,571 A | 5/1995 | Katsaros et al. | |
| 5,496,332 A | 3/1996 | Sierra et al. | |
| 5,545,178 A | 8/1996 | Kensey et al. | |
| 5,593,422 A | 1/1997 | Muijs Van de Moer et al. | |
| 5,620,461 A | 4/1997 | Muijs Van De Moer et al. | |
| 5,630,833 A | 5/1997 | Katsaros et al. | |
| 5,690,674 A | 11/1997 | Diaz | |
| 5,700,277 A | 12/1997 | Nash et al. | |
| 5,749,883 A | 5/1998 | Halpern | |
| 5,766,220 A | 6/1998 | Moenning | |
| 5,797,933 A | 8/1998 | Snow et al. | |
| 5,826,251 A | 10/1998 | Kiendl | |
| 5,944,730 A | 8/1999 | Nobles et al. | |
| 6,168,623 B1 | 1/2001 | Fogarty et al. | |
| 6,171,319 B1 | 1/2001 | Nobles et al. | |
| 6,214,022 B1 * | 4/2001 | Taylor et al. ............ 606/153 |
| 6,248,119 B1 | 6/2001 | Solem | |

(Continued)

FOREIGN PATENT DOCUMENTS

EP    0 544 485 A1    6/1993

(Continued)

Primary Examiner—Patricia Bianco
(74) Attorney, Agent, or Firm—Fenwick & West LLP

(57) ABSTRACT

Surgical construction or bypass grafting of a target vessel includes method and instrumentation and apparatus for forming and inserting a fluid-impervious tubular conduit including a central protrusion through an aperture in the vessel to form a fluid-conducting shunt past the aperture. An anastomosis over the aperture is partially completed with the protrusion of the tubular conduit extending through the partial anastomosis. A removal tube is disposed over the protrusion for applying tensile force thereto relative to the tubular conduit for dissembling the tubular conduit along a continuous path for removal as a single strand from the vessel through the tube and aperture and the partial anastomosis prior to completion of the procedure.

8 Claims, 3 Drawing Sheets

U.S. PATENT DOCUMENTS 6,395,015 B1   5/2002   Borst et al.
6,409,739 B1   6/2002   Nobles et al.
6,464,712 B1   10/2002  Epstein et al.

FOREIGN PATENT DOCUMENTS

EP   0 894 475 A1 *  2/1999

* cited by examiner

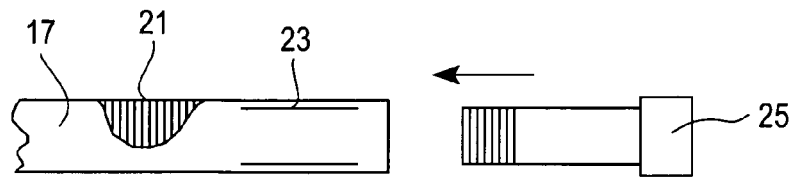
FIG. 6A
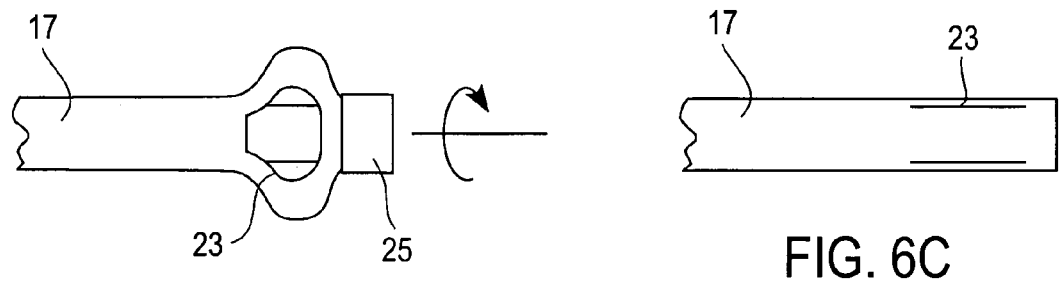
FIG. 6B
FIG. 6C
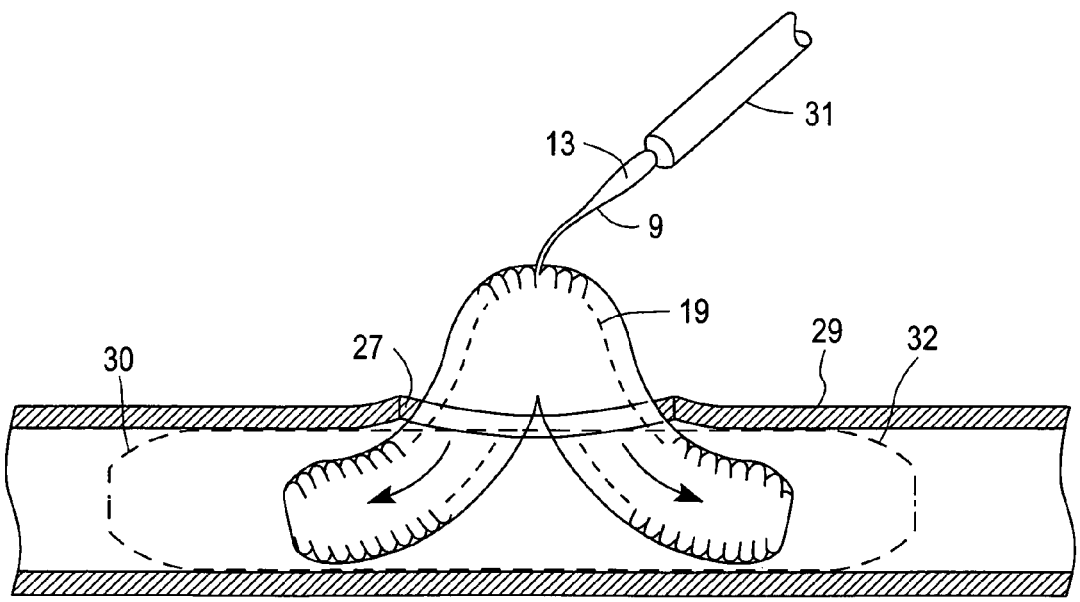
FIG. 8

TEMPORARY ARTERIAL SHUNT AND METHOD

FIELD OF THE INVENTION

This invention relates to temporary conduits for use in vascular surgical procedures, and more particularly to a temporary shunt for easy insertion into, and removal from, a target vessel in a living body.

BACKGROUND OF THE INVENTION

During arterial reconstruction or bypass procedures, the target artery is generally clamped proximal and distal to an anastomotic site for a brief interval to provide a blood-free field for performing the anastomosis. However, interruption of blood flow in the recipient artery may be dangerous to the patient. Ischemia to the heart during coronary artery bypass may result in myocardial infarction. Similarly, ischemia to the brain during carotid endarterectomy may result in stroke. Consequently, surgeons often place an arterial shunt in the artery undergoing reconstruction, to avoid the potential for ischemic complications. The arterial shunt is a flexible tube that is inserted into the arteriotomy. The outer diameter of the shunt approximates the inner diameter of the artery, so that flow is maintained in the artery and ischemia does not occur as the arterial bypass or endarterectomy is being performed.

Presently, it is difficult to remove a shunt following its use. As the anastomosis is being completed, or the artery is being closed following endarterectomy, the last several suture loops at the entry site of the shunt are not cinched down, and the shunt is worked out of the artery. Shunt removal is a delicate process, and it may be difficult to perform without disrupting the anastomosis being formed. The anastomotic suture may be broken, or tension on the suture may cause it to cut through the arterial wall.

SUMMARY OF THE INVENTION

In accordance with an embodiment of the present invention, a shunt is formed of a coiled strand, with a loop of the strand extending out of the center of the formed shunt. A tube is positioned over the center loop against the shunt to aid in removing the shunt by uncoiling the coiled strand for retrieval through the tube. The distal ends of the shunt may contain bulbous portions formed out of the strand to enhance fluid-tight sealing of the shunt within the inner walls. Alternatively, the coiled strand may form a tapered shunt, with one end of greater diameter than the other end.

In use, the shunt is placed into an incision in a vessel, with one end of the shunt contacting the inner wall of the vessel proximal to the incision and the other end of the shunt contacting the inner wall of the vessel distal to the incision. The anastomosis is sewn with only the loop extending out of the anastomotic attachment. A stitch is placed on either side of the loop as it exits the intra-vessel portion of the shunt. At the completion of the anastomosis, before the ends of the suture are tied, the removal tube is brought down to the vessel surface, and held stationary with a pair of curved or right-angled clamps. The loop of the shunt is pulled against the tube to cause the shunt to dissemble and peel away into a strand for removal through the tube. The stationary tube rests against the outer surface of the shunt during the dissembly process to assure that the suture line is not stressed as tensile force is exerted on the loop to unravel and remove the shunt. In this way, substantially all the force required to disassemble the shunt is exerted against the distal end of the tube.

BRIEF DESCRIPTION OF THE DRAWINGS

FIGS. 6a–6c are partial plan views of a mandrel for forming bulbous ends on a shunt in accordance with an embodiment of the present invention;

FIG. 8 is a sectional view of the shunt being inserted into an artery.

DETAILED DESCRIPTION OF THE INVENTION

Figure 1:
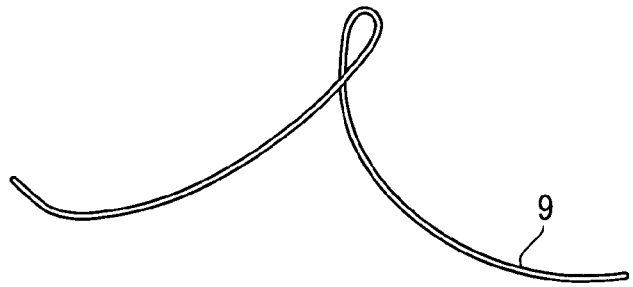
FIG. 1 is a perspective view of a flexible tensile element such as a suture coated with a thermoplastic polymer.

Referring now to FIGS. 1–4, there is shown an embodiment of the present invention in which a tubular conduit for use as an arterial shunt is formed as a coil including a plurality of substantially contiguous convolutes 16 of an elongated strand 9 that may be coated with a bioinert and preferably thermoplastic polymer. The strand 9 is wound on a mandrel 17 that has a substantially constant diameter between the ends thereof, with a protruding loop 13 formed intermediate the ends. The strand 9 is constructed from a length of suture or wire that is coated with a material such as polyvinyl chloride, polyurethane, silicone rubber, or the like. The center of the length of strand 9 is formed into the loop 13 of length approximately 5 cm. The two strands at the bottom of the loop 13 may be held together by a tie 15 such as a band heat-sealed to the strands, or by a length of heat shrink tubing, or by a suture winding, or held together by adhesive, or by welding a length of adjacent strands together using heat or solvent bonding, or the like.

Figure 2:
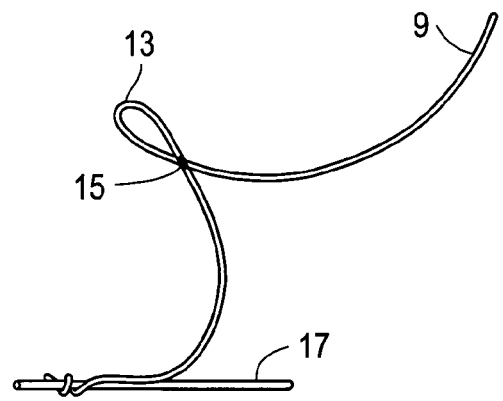
FIG. 2 is a perspective view of the tensile element of FIG. 1 being formed around a mandrel.
Figure 3:
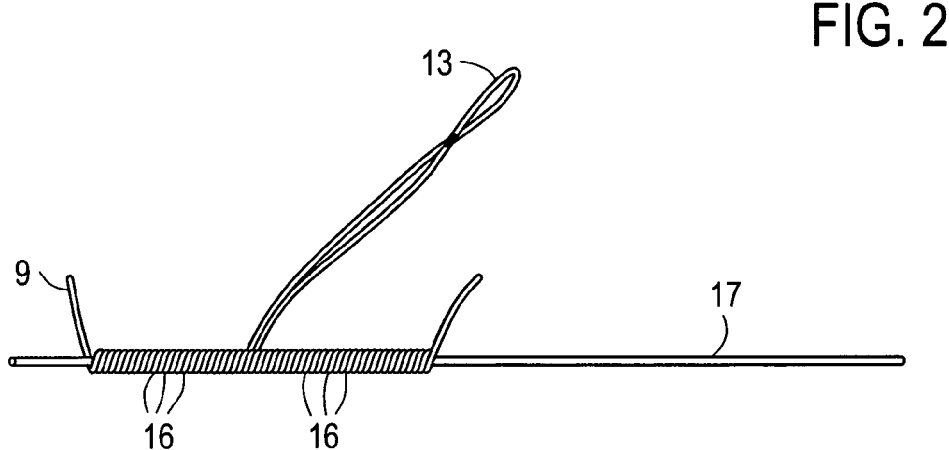
FIG. 3 is a perspective view of the tensile element coiled about the mandrel.
Figure 4:
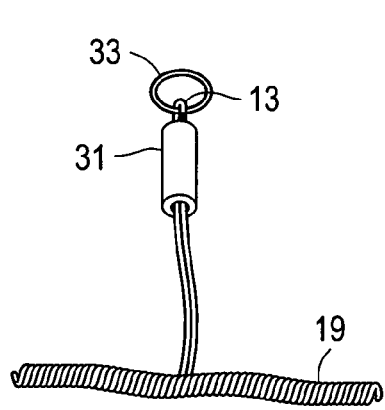
FIG. 4 is a perspective view of the shunt formed from the fused tensile element.

The strand 9 with its formed center loop 13 is continuously wound around a rod-like mandrel 17, as shown in FIGS. 2 and 3, with adjacent convolutes 16 of the coil substantially in contact with one another. The ends of the strand 9 are temporarily held onto the mandrel 17 using clips, clamps, elastic bands, sutures, or the like, as shown in FIG. 3. The adjacent convolutes 16 of the continuously coiled and looped strand 9 are then bonded together by heating and pressing the thermoplastic coating, or by adhesive bonding or solvent bonding or by surface coating, or the like, to form the tubular, liquid-impervious conduit 19 that serves as the arterial shunt, as shown in FIG. 4. Expanded bulbous ends may be formed on the distal ends of the conduit or shunt by expanding a corresponding portion of the mandrel 17, as shown in FIGS. 6a–6c, prior to winding and bonding of the coiled and looped strand. The ends of the mandrel 17 may then be contracted to allow release of the bonded shunt 19.

The conduit or shunt 19 may also be formed with varying pitch of adjacent convolutes 16 along the tubular length thereof to promote varied flexibility between the ends. As shown, for example, in FIG. 8, greater bending occurs near the center and ends as the shunt 19 is inserted into the artery or vessel 29. Also, the shunt 19 may be formed of the strand wound in opposite directions between the protrusion and each end, or may be formed with tapering cross section between the ends, for example, to establish a selected pressure drop through the shunt where desirable in certain surgical environments. Additionally, shunt 19 may be formed of a strand 9 that is disposed, for example, along a serpentine pattern from end to end, or from center to each end, about the entire periphery of the tubular shunt 19. Also, the loop 13 may be disposed closer to one of the spaced ends to facilitate easier insertion of the shunt into an artery. In another embodiment, the ends of the strand 9 may be routed through the tubular conduit 19 from the spaced ends to be brought out through a central portion of the tubular conduit 19 as the protrusion on which tensile force is exerted in order to disassemble the shunt inwardly from the spaced ends toward the center.

In each such form of the shunt 19, the region between adjacent convolutes or wraps of the strand constitutes a continuous region of diminished tensile and shear strength whether formed by heating and pressing together of a thermoplastic surface layer, or by surface coating, or by adhesive or welded attachment of the adjacent convolutes in order to assure that disassembly of the tubular shunt occurs along such region, as later described herein.

Referring now to the partial plan views of FIGS. 6a–6c, the expandable end portions of the mandrel 17 may be constructed as lengths of longitudinally split tube 23 with an internally threaded portion 21 proximal to the split portions 23. Bolts 25 threaded into the ends of the mandrel 17 compress the split portions 23 of the mandrel and cause them to expand. Formation of the mandrel from resilient material allows the mandrel 17 to contract to its natural, undilated position. Upon removal of the threaded bolts 25, the associated tubular conduit 19 thus formed around such expandable mandrel 17 includes bulbous extreme ends that promote superior liquid sealing against the arterial walls when positioned within the target artery. A removal tube 31 may be captivated overlaying the loop 13 by attaching a ring 33 through the loop 13 of the larger diameter than can pass through the removal tube 31.

Figure 7:
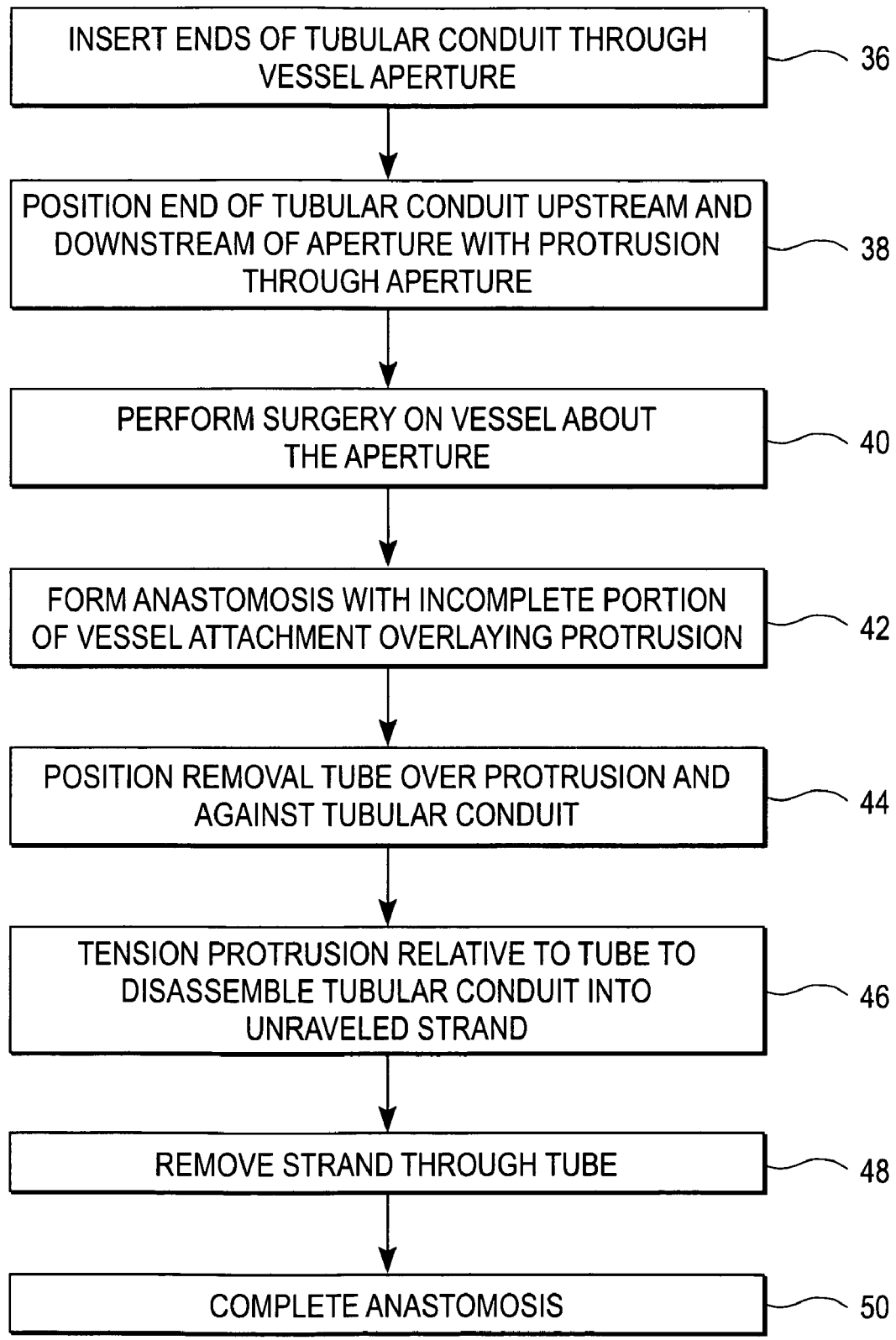
FIG. 7 is a flow chart illustrating the process of installing and removing a temporary shunt in accordance with an embodiment of the present invention.

In operation, and with reference to the flow chart of FIG. 7 and the sectional view of FIG. 8, the tubular conduit 9 is sufficiently flexible and resilient when formed as previously described to facilitate reasonably easy insertion 36 of the ends through an aperture 27 in a wall of artery or vessel 29. Then, by manipulating extension of the remote ends of the tubular conduit 19 into upstream and downstream positions 30, 32 relative to the vascular aperture 27, the tubular conduit 19 can be so positioned 38 to serve as a vascular shunt through the region of the aperture 27 to promote continued blood flow through the inside of the convolutes during vascular surgery 40 for the reconstruction or formation of a vascular bypass on the target vessel 29. The integral loop 13 remains protruding through the vascular aperture 27 and through a partially completed anastomosis 42 (not shown) to facilitate later removal of the shunt 19 from within the vessel 29.

Figure 5:
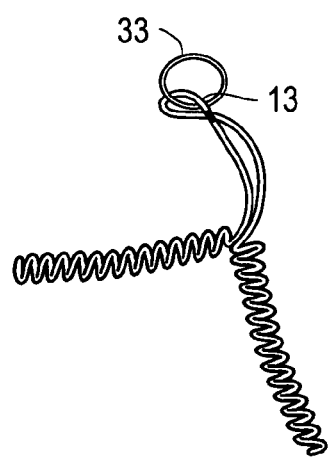
FIG. 5 is a perspective view of the dissembled shunt as retrieved through a removal tube.

In an arterial bypass anastomosis or arterial reconstruction, and before first and last stitches of the suture are tied off, the central loop 13 remains protruding through the incomplete segment of the anastomosis to facilitate convenient removal of the shunt with minimal disturbance of surrounding tissue. Specifically, a removal tube 31, as shown in FIGS. 4 and 8, is positioned 44 over the central loop 13 against the shunt 19, with the distal end of the removal tube 31 disposed between first and last stitches in the incomplete segment of the anastomosis. The loop 13 is then tensioned 46 relative to the removal tube 31, which can be retained in fixed position relative to the artery 29, in order to unravel the shunt 19 for removal 48 from within the artery through the removal tube 31 as the looped, continuous strand 9, as shown in FIG. 5. Removal of the strand 9 and associated liquid-impervious layer thereon through the removal tube 31 in this manner thus minimizes dissociative forces applied to the target artery 29 or the anastomosis which can then be completed 50 by tightening the sutures and tying off the ends, with resultant minimum loss of blood or interruption of arterial blood flow.

Therefore, the method and apparatus of the present invention provide a temporary shunt to facilitate blood flow through a target vessel during vascular reconstruction or bypass surgery. Various configurations of the tubular conduit facilitate insertion and removal of the shunt with minimum blood loss or interruption of blood flow.

What is claimed is:

1. A temporary sealing element for forming a fluid-tight conduit within a fluid conduit within a patient's body, the temporary sealing element comprising:
   a tubular conduit having spaced ends and a protrusion formed intermediate the spaced ends, the tubular conduit including a region of diminished shear strength extending along a continuous path on the tubular conduit from the protrusion to each of the spaced ends thereof for selectively disassembling the tubular conduit along the continuous path in response to tension applied to the protrusion to disassemble the tubular conduit into at least one continuous strand along the path from the protrusion to an end spaced therefrom.

2. The temporary sealing element according to claim 1 including a strand of material forming the protrusion and a plurality of contiguous convolutes disposed along the tubular conduit between the spaced ends thereof, with successive convolutes extending remotely from the protrusion to the spaced ends, and with each convolute adhering to adjacent convolutes in regions therebetween of said diminished shear strength extending along the continuous path on the tubular conduit.

3. The temporary sealing element according to claim 2 in which the strand of material that forms the protrusion and tubular conduit includes bioinert thermoplastic material and includes thermoplastic adhesion between contiguous edges of adjacent convolutes of the strand disposed in a helical pattern forming the tubular conduit.

4. The temporary sealing element according to claim 3 in which said bioinert thermoplastic material is polyvinyl chloride.

5. The temporary sealing element according to claim 2 including a removal tube overlaying the protrusion and selectively positionable against the tubular conduit to facilitate exertion of tensile force on the protrusion relative to the removal tube in position against the tubular conduit for disassembling the tubular conduit along the continuous path.

6. The temporary sealing element according to claim 1 in which
   the tubular conduit is formed of flexible resilient material and includes a generally cylindrical cross section between the spaced ends, and the protrusion is integrally formed therewith.

7. The temporary sealing element according to claim 6 in which
   the region of diminished shear strength extends from the protrusion along a meandering path to the spaced ends of the tubular conduit.

8. The temporary sealing element according to claim 6 in which the region of diminished shear strength extends from the protrusion along a substantially helical path to the spaced ends of the tubular conduit.

* * * * *